United States Patent [19]

Sugiyama et al.

[11] Patent Number: 4,964,853

[45] Date of Patent: Oct. 23, 1990

[54] CATHETER EQUIPPED WITH EXPANSIBLE MEMBER

[75] Inventors: Yoshiaki Sugiyama; Kyuta Sagae, both of Kanagawa, Japan

[73] Assignee: Terumo Kabushiki Kaisha, Tokyo, Japan

[21] Appl. No.: 415,345

[22] PCT Filed: Feb. 25, 1988

[86] PCT No.: PCT/JP88/00201

§ 371 Date: Oct. 26, 1989

§ 102(e) Date: Oct. 26, 1989

[87] PCT Pub. No.: WO88/06464

PCT Pub. Date: Sep. 7, 1988

[30] Foreign Application Priority Data

Feb. 27, 1987 [JP] Japan .................................. 62-46196

[51] Int. Cl.$^5$ ............................................ A61M 25/00
[52] U.S. Cl. .................................... 604/96; 604/102
[58] Field of Search .................. 604/96, 102, 93, 103, 604/280, 264, 43–45

[56] References Cited

U.S. PATENT DOCUMENTS

4,195,637  4/1980  Gruntzig et al. .
4,323,071  4/1982  Simpson et al. .
4,411,055  10/1983 Simpson et al. .
4,597,755  7/1986  Samson et al. ........................ 604/96
4,752,286  6/1988  Okada ............................... 604/102 X
4,762,129  8/1988  Bonzel .............................. 604/96 X
4,892,099  1/1990  Ohkawa et al. .................... 604/96 X Primary Examiner—John D. Yasko
Attorney, Agent, or Firm—Frishauf, Holtz, Goodman & Woodward

[57]         ABSTRACT

A catheter equipped with an expansible member comprising an inner tube having a first lumen whose tip is open and a second lumen extending to the tip direction of the first lumen; an outer tube disposed coaxially with the inner tube and having a tip at a position recessed by a predetermined distance from the tip of the inner tube and forming a third lumen between it and the outer surface of the inner tube; a contractible or foldable expansible member having a tip end portion and a base end portion, the base end portion being fitted to the outer tube and the tip end portion being fitted to the inner tube, the expansible member communicating with the second lumen near the tip end portion and with the third lumen near the base end portion; a first opening communicating with the first lumen and a second opening communicating with the second lumen each disposed at the base end portion of the inner tube; and a third opening disposed at the base end portion of the outer tube and communicating with the third lumen.

2 Claims, 5 Drawing Sheets

CATHETER EQUIPPED WITH EXPANSIBLE MEMBER

DESCRIPTION

1. Technical Field

This invention relates to a catheter equipped with an expansible member for use in curing a stricture portion inside a blood vessel. Specifically, this invention relates to a catheter equipped with an expansible member for expanding a stricture portion inside a blood vessel to improve the blood flow on the peripheral side of the stricture portion.

2. Background Art

Heretofore, as a catheter equipped with an expansible member for expanding a stricture portion of a blood vessel, there has been so-called Gruentich type disclosed, for example, in U.S. Pat. No. 4,195,637. Further, there has been used so-called Simpson-Robert type disclosed, for example, in U.S. Pat. No. 4,323,071.

Previously, adaptible cases of vasodilatation were limited to cases of localized stricture near coronary artery from an anatomical viewpoint, which were lesions of about 15 to 20 mm length, monobranched lesions, non-calcified lesions, etc. In order to extend more the range of adaptible cases, as the above type catheter, a catheter equipped with an expansible member of low-profile shape having the same structure but narrowed only at the tip has been considered in addition to those of standard structure to be adaptible to strictures in more peripheral blood vessel or severer strictures (sub-complete clogging).

A catheter called Gruentich type as described above comprises a catheter tube having two lumens and an expansible member attached near the tip of the catheter tube. One of the lumens is open at the tip of the catheter to form a channel for a guide wire and for tip pressure measurement. The other of the lumens is in communication with the inside of the expansible member at the base end of the expansible member to form a flow channel for injecting fluid for expansion such as vasographic contrast liquid under pressure to expand the expansible member. In this catheter, it is difficult to remove bubbles remaining within the expansible member when expanded by injecting vasographic contrast liquid or the like into the expansible member. If bubbles remain, X-ray image may become unclear and the remaining bubbles may enter the human body in the case that the expansible member is damaged from some cause.

A catheter called Simpson-Robert type has a coaxial double-wall structure comprising an inner tube forming a first lumen whose tip is open, and an outer tube into which the inner tube is inserted and to the tip of which an expansible member is attached. A second lumen is formed between the inner surface of the outer tube and the outer surface of the inner tube. An ultrafine metal pipe is disposed in the second lumen for removing bubbles. Although bubbles do not remain in the catheter of this type unlike those called Gruentich type as described above, because the metal pipe is used, the catheter of this type has little followabilty to the shape and movement of a blood vessel which is intensely curved. Further, the metal pipe inserted may injure or damage the inner wall of the catheter or expansible member.

Accordingly, an object of the present invention is to provide a catheter equipped with an expansible member in which it is easy to remove bubbles from the inside of the expansible member and there is no worry of damaging the catheter or expansible member.

DISCLOSURE OF THE INVENTION

A catheter equipped with an expansible member according to the present invention comprises an inner tube having a first lumen whose tip is open and a second lumen extending to the tip direction of the first lumen; an outer tube disposed coaxially with the inner tube and having a tip at a position recessed by a predetermined distance from the tip of the inner tube and forming a third lumen between it and the outer surface of the inner tube; a contractible or foldable expansible member having a tip end portion and a base end portion, the base end portion being fitted to the outer tube and the tip end portion being fitted to the inner tube, the expansible member communicating with the second lumen near the tip end portion and with the third lumen near the base end portion; a first opening communicating with the first lumen and a second opening communicating with the second lumen each disposed at the base end portion of the inner tube; and a third opening disposed at the base end portion of the outer tube and communicating with the third lumen.

BEST MODE FOR PRACTICING THE INVENTION

A catheter equipped with an expansible member according to the present invention will be described with reference to a preferred embodiment shown in the drawings.

Figure 1:
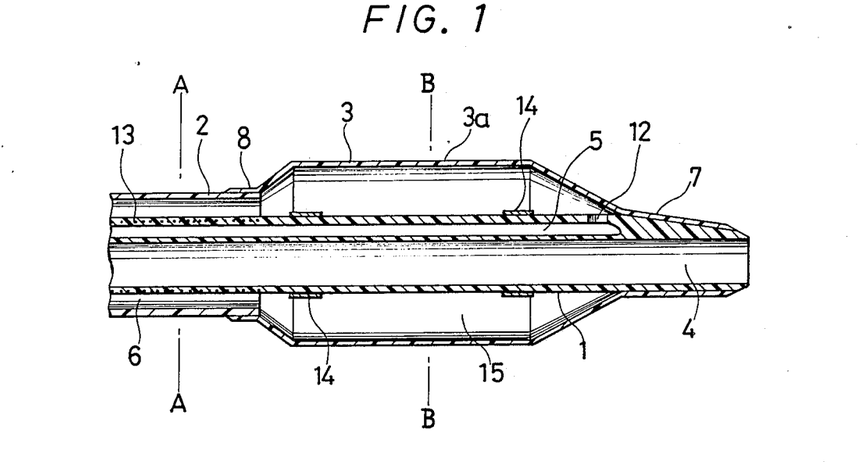
FIG. 1 is an enlarged cross sectional view of the tip end portion of one embodiment of a catheter equipped with an expansible member according to the present invention.
Figure 2:
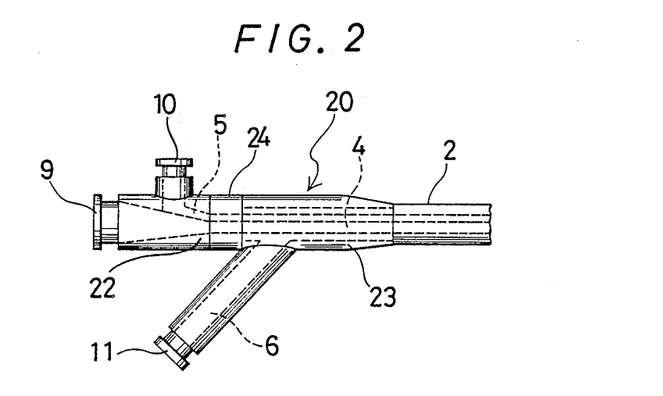
FIG. 2 is a view showing the base end portion of one embodiment of a catheter equipped with an expansible member according to the present invention.

FIG. 1 is an enlarged cross sectional view of the tip end portion of one embodiment of a catheter equipped with an expansible member according to the present invention and FIG. 2 is a view showing the base end portion of the catheter.

A catheter equipped with an expansible member according to the present invention comprises an inner tube 1 having a first lumen 4 whose tip is open and a second lumen 5 extending to the tip direction of the first lumen; an outer tube 2 disposed coaxially with the inner tube 1 and having a tip at a position recessed by a predetermined distance from the tip of said inner tube and forming a third lumen 6 between it and the outer surface of the inner tube 1; a contractible or foldable expansible member 3 having a tip end portion 7 and a base end portion 8, the base end portion 8 being fitted to the outer tube 2 and the tip end portion 7 being fitted to the inner tube 1, said expansible member communicating with the second lumen 5 near the tip end portion and with the third lumen 6 near the base end portion; a first opening 9 communicating with the first lumen 4 and a second opening 10 communicating with the second lumen 5 each disposed at the base end portion of the inner tube 1; and a third opening 11 disposed at the base end portion of the outer tube 2 and communicating with the third lumen 6.

Hereinafter, the explanation will be made with reference to the drawings.

A catheter equipped with an expansible member according to the present invention comprises a catheter main body including an inner tube 1, an outer tube 2 and an expansible member 3, and a branched hub 20.

Figures 3, 4:
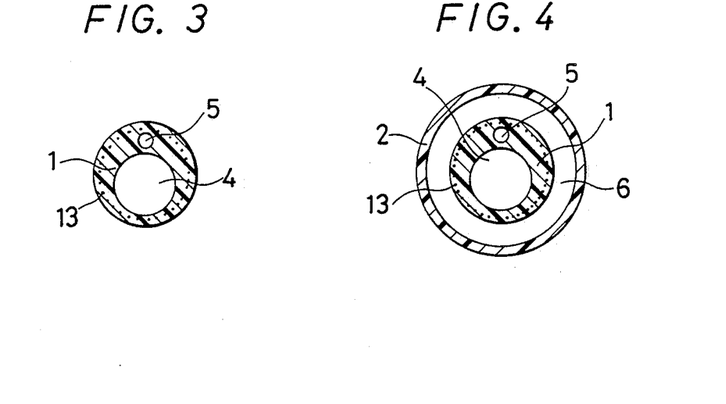
FIG. 3 is a cross sectional view of the inner tube of the catheter equipped with the expansible member shown in FIG. 1.
FIG. 4 is a cross sectional view of the catheter equipped with the expansible member taken along line A—A of FIG. 1.

The inner tube 1 has a first lumen 4 whose tip is open and a second lumen 5 which is formed in parallel with the first lumen 4 and whose tip is closed. The first lumen 4 is a lumen for inserting a guide wire therein and in communication with a first opening 9 which forms a guide wire port disposed in the branched hub 20 described later. The second lumen 5 is a lumen for removing bubbles from the inside of the expansible member 3 described later and in communication with the expansible member 3 through a side hole 12. The rear end of the second lumen is in communication with a second opening 10 which forms a vent port disposed in the branched hub 20. The shape of the tip portion of the second lumen is not limited to that of the closed end as shown in FIG. 1 but may be, for example, a shape in which the tip of the second lumen is bent to the direction of the inside of the expansible member. The second lumen 5 is formed in the inner wall of the inner tube 1 as shown in FIG. 1 and FIG. 3 which is a cross section of the inner tube, and has the inner diameter smaller than the first lumen.

The inner tube 1 has the outer diameter of 0.50 to 2.50 mm, preferably 0.55 to 2.40 mm. The inner diameter of the first lumen is 0.25 to 1.60 mm, preferably 0.30 to 1.50 mm. The inner diameter of the second lumen is 0.03 to 0.20 mm, preferably 0.04 to 0.15 mm. The shape of the cross section of each of the first and second lumens is not limited to circle.

The diameter of the tip portion of the inner tube 1 is preferably reduced in a tapered shape toward the tip. In the embodiment shown in FIG. 1, the diameter of the tip portion of the inner tube 1 is taperingly reduced at a thick portion at which the second lumen 5 is formed. The reason thereof is that such a taper makes the catheter easy to be inserted into a stricture portion in a blood vessel.

The second lumen may not be formed within the thickness of the inner tube. For example, a tube body forming the second lumen may be mounted to the outer surface of a tube body having the first lumen to form an inner tube.

The material for forming the inner tube 1 preferably has a certain extent of flexibility. For example, there are usable thermoplastic resin such as polyolefin such as polyethylene, polypropylene, ethylene-propylene copolymer and ethylene-vinyl acetete copolymer, polyvinyl chloride, polyamide elastomer and polyurethane; silicone rubber, latex rubber, etc. The thermoplastic resin is preferable and the polyolefin is more preferable.

Further, the inner tube 1 is preferably provided with a rigidity imparting member 13. The rigidity imparting member 13 is for preventing collapse of the catheter main body at its bent portion and, further, improving the torque transmission efficiency of the catheter main body. By disposing the rigidity imparting member 13, collapse of the catheter main body at its bent portion can be prevented and, further, the torque transmission efficiency of the catheter main body can be improved and when the catheter main body is moved and rotated in a delicate fashion at the base end portion of the catheter main body, the torque and the enforcing force can be surely transmitted to the tip portion of the catheter main body, and the tip portion of the catheter main body and further the expansible member disposed on the tip portion can be easily introduced into a highly stricture portion in a blood vessel. The rigidity imparting member 13 is preferably disposed at least from the base end of the inner tube 1 to the vicinity of the tip portion of the outer tube 2. The rigidity imparting member may be disposed over the entire length of the inner tube 1 for improving the torque and force transmission efficiencies. In the case of disposing the rigidity imparting member on the whole of the inner tube, it is preferable that only the tip portion of the inner tube is a portion in which the rigidity imparting member is not disposed so as to prevent the end of the rigidity imparting member from protruding beyond the tip portion of the inner tube. The end of the expansible member does not protrude beyond the tip of the inner tube and the inner wall of a blood vessel can be prevented from being damaged.

The rigidity imparting member 13 is preferably a mesh-like rigidity imparting member. The mesh-like rigidity imparting member is preferably a braided member made of a wire material, particularly a metal wire. As the metal wire, there is suitably used a metal wire made of, for example, stainless steel, elastic metal, super elastic alloy, shape memory alloy, etc. of the wire diameter of 0.01 to 0.2 mm, preferably 0.03 to 0.1 mm. The mesh-like rigidity imparting member can be formed by winding such a metal wire as described above on the outer surface of the inner tube 1 in a mesh-like manner. Further, the rigidity imparting member formed on the outer surface of the inner tube 1 is preferably embedded in the outer wall of the inner tube 1 to make the outer surface smooth. This measure can be taken place by forming an inner tube 1 with a thermoplastic resin, and after winding the rigidity imparting member described above, heating the inner tube 1 from the outside (for example, by inserting the inner tube into a heating dice) and embedding the rigidity imparting member in the outer wall of the inner tube.

The rigidity imparting member is not limited to metal wire but may be formed by the manner that a synthetic fiber such as a polyamide fiber, a polyester fiber and a polypropylene fiber is wound on the outer surface of the inner tube 1.

The outer tube 2 into which the inner tube 1 is inserted has a tip slightly recessed by a predetermined distance from the tip of the inner tube. As shown in FIG. 4 which is a cross section taken along line A—A in FIG. 1, a third lumen 6 is formed by the inner surface of the outer tube 2 and the outer surface of the inner tube 1. Thus, the third lumen is a lumen having a sufficient volume. The tip of the third lumen 6 is in communication with the rear end portion of the inside of the expansible member 3. The rear end of the third lumen 6 is in communication with a third opening 11 of the branched hub 20 forming an injection port for injecting fluid for expanding the expansible member (for example, vasographic contrast liquid).

The material for forming the outer tube 2 preferably has a certain extent of flexibility. For example, there are usable thermoplastic resin such as polyolefin such as polyethylene, polypropylene, ethylene-propylene copolymer and ethylene-vinyl acetete copolymer, polyvinyl chloride, polyamide elastomer and polyurethane; silicone rubber, latex rubber, etc. The thermoplastic resin is preferable and the polyolefin is more preferable.

Further, instead of providing the rigidity imparting member to the inner tube, the outer tube may be provided with a rigidity imparting member. By disposing the rigidity imparting member, collapse of the catheter main body at its bent portion can be prevented and, further, the torque transmission efficiency of the catheter main body can be improved. As the rigidity imparting member, those described in relation to the inner tube 1 can be suitably used. Further, it is preferable that the rigidity imparting member formed on the outer surface of the outer tube is embedded in the outer wall of the outer tube to make the outer surface smooth. By making the outer surface of the outer tube smooth, it can be alleviated that clogs generate on the outer surface of the catheter and the inner wall of a blood vessel is damaged. Rigidity imparting members may be disposed to both of the inner and outer tubes 1 and 2.

The outer tube 2 has the outer diameter of 0.95 to 4.30 mm, preferably 1.00 to 4.00 mm and the inner diameter of 0.70 to 3.80 mm, preferably 0.80 to 3.00 mm. Further, the difference between the outer diameter of the inner tube 1 and the inner diameter of the outer tube 2 is 0.20 to 3.30 mm, preferably 0.50 to 1.50 mm.

Figure 5:
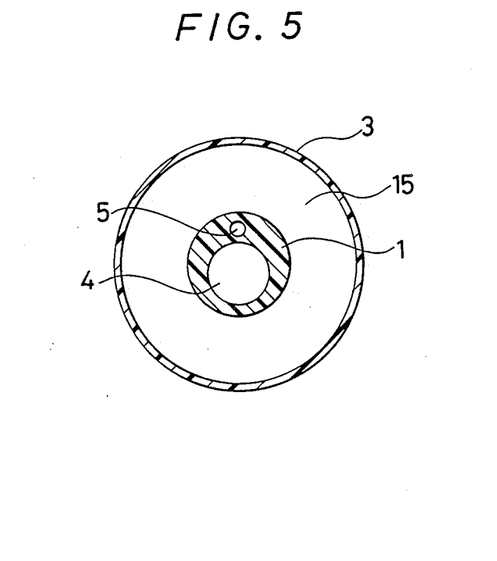
FIG. 5 is a cross sectional view of the catheter equipped with the expansible member taken along line B—B of FIG. 1.

The expansible member 3 is contractible or foldable and it is contracted or folded on the outer circumference of the inner tube 1 in its non-expanded state. The expansible member 3 has a portion at least a part of which is substantially cylindrical for enabling to expand a stricture portion in a blood vessel, and in the embodiment shown in FIG. 1, it has a substantially cylindrical portion 3a having the approximately uniform diameter. The substantially cylindrical portion described above may not be completely cylindrical but may be polygonal. The rear end portion 8 of the expansible member 3 is secured in a liquid-tight manner to the tip portion of the outer tube 2 by adhesion, fusion or the like. The tip portion 7 is secured in a liquid-tight manner to the tip portion of the inner tube 1 by the similar manner. As shown in FIG. 5 showing a cross section of the catheter equipped with the expansible member taken along line B—B in FIG. 1, the expansible member 3 forms an expanded space 15 between the inner surface of the expansible member 3 and the outer surface of the inner tube 1. The expanded space 15 is in communication at its tip portion with the second lumen 5 through the side hole 12 of the inner tube 1 and over the entire circumference at its rear end portion with the third lumen 6. Thus, the third lumen 6 having a relatively large volume is in communication with the rear end of the expansible member 3 and the second lumen 5 is in communication with the tip portion of the expansible member 3. Therefore, when expansion fluid is injected through the third lumen 6 into the expansible member 3, air within the third lumen 6 and further within the expansible member 3 is replaced by the fluid injected in accordance with the inflow of the fluid. The air flows out to the outside through the second lumen 5 so that the air within the catheter main body can be easily removed.

The material for forming the expansible member 3 preferably has a certain extent of flexibility. For example, there are usable thermoplastic resin such as polyolefin such as polyethylene, ethylene-propylene copolymer, ethylene-vinyl acetete copolymer and cross-linked ethylene-vinyl acetete copolymer, polyvinyl chloride, polyamide elastomer, polyester and polyurethane; silicone rubber, latex rubber, etc. The above thermoplastic resin is preferable and the cross-linked ethylene-vinyl acetete copolymer is more preferable. Further, the forward and backward portions of the cylindrical portion 3a of the expansible member 3 extending to the secured portions 7 and 8 to the inner and outer tubes 1 and 2 described above are tapered.

As the size of the expansible member 3, the cylindrical portion upon expanded has the outer diameter of 1.50 to 35.00 mm, preferably 2.00 to 30.00 mm and the length of 5.00 to 80.00 mm, preferably 10.00 to 75.00 mm. The entire length of the expansible member 3 is 10.00 to 120.00 mm, preferably 15.00 to 100.00 mm.

It is preferable that markers 14 made of X-ray impermeable material (for example, gold, platinum or alloy thereof) are provided on the portions near the base end of the side hole 12 and nearer to the tip side than the secured portion of the expansible member 3 to the outer tube 2 and located at both ends of the cylindrical portion 3a of the expansible member 3. This is for enabling to confirm easily the position of the expansible member 3 under X-ray perspection. The form of the marker 14 is a ring made of metal described above and calked onto the outer surface of the inner tube 1.

Further, in the catheter equipped with the expansible member according to the present invention, it is preferable for facilitating the insertion into a blood vessel and further into a guide catheter described later to apply hydrophilic treatment to portions which can come into contact with blood in operation, that is, the outer surfaces of the outer tube 2 and expansible member 3 so as to have lubricancy. As such hydrophilic treatment, there can be mentioned a method of coating a hydrophilic polymer, for example, poly(2-hydroxyethylmethacrylate), polyhydroxyethylacrylate, hydroxypropylcellulose, methyl vinyl ether-maleic anhydride copolymer, polyethylene glycol, polyacrylamide, polyvinyl pyrrolidone, etc.

As shown in FIG. 2, the branched hub 20 comprises an inner tube hub 22, an outer tube hub 23 and a sealing member 24. The inner tube hub 22 has an first opening 9 forming a guide wire port and a second opening 10 forming a vent port, and is secured to the base end portion of the inner tube 1. The first opening 9 is in communication with the first lumen 4 of the inner tube 1 and the second opening 10 is in communication with the second lumen 5 of the inner tube 1. The outer tube 23 is secured to the base end portion of the outer tube 2 and has a third opening 11 forming an injection port. The third opening 11 is in communication with the third lumen 6. The sealing member 24 is disposed between the inner and outer tube hubs 22 and 23 to seal the rear end portion of the outer tube hub 23. These three members of the inner and outer tube hubs 22 and 23 and sealing member 24 are secured to one another.

For the material for forming the branched hub, there can be suitably used thermoplastic resin such as polycarbonate, polyamide, polysulfone, polyarylate and methacrylate-butylene-styrene copolymer. Instead of providing such a branched hub, for example, a tube having a port member forming an opening at its rear end may be attached in a liquid-tight manner to each of the first, second and third lumens.

Next, the operation of the catheter equipped with the expansible member according to the present invention will be described with reference to explanatory views shown in FIGS. 6 to 10 using the catheter equipped with the expansible member of the embodiment shown in FIGS. 1 to 5.

Before administering a dilatating cure of a stricture portion which has occurred in a blood vessel, air within the catheter equipped with the expansible member is removed. For this purpose, the tip of the catheter according to the present invention is turned upwards, X-ray contrast liquid is injected through the third opening 11, the vasographic contrast liquid is made to flow from the base end side of the third lumen 6 to the inside of the third lumen 6 and further to the inside of the expansible member 3, and the inside of the lumen 6 and the inside of the expansible member 3 are filled with the vasographic contrast liquid. The air within the expansible member 3 is made to flow through the side hole 12, second lumen 5 and second opening 10 to the outside in accordance with the inflow of the contrast liquid. The confirmation of the removal of the air from the inside of the catheter equipped with the expansible member can be made with the contrast liquid flowing out of the second opening 10. After confirming the removal of the air, the opening 10 is closed with a cap (not shown).

Figure 6:
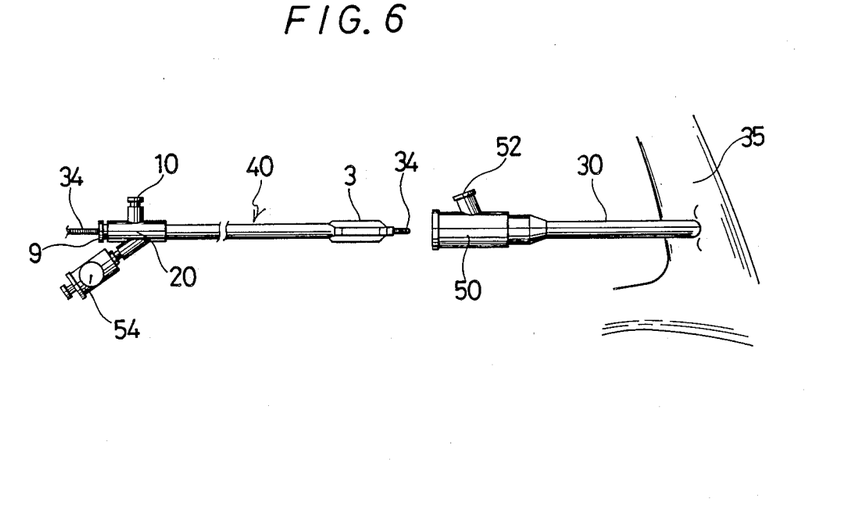
FIGS. 6, 7, 8, 9 and 10 are explanatory views for illustrating the operation of the catheter equipped with the expansible member according to the present invention.
Figure 7:
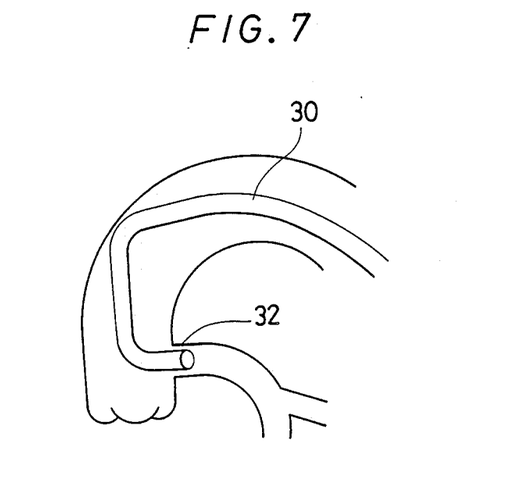
Figure 8:
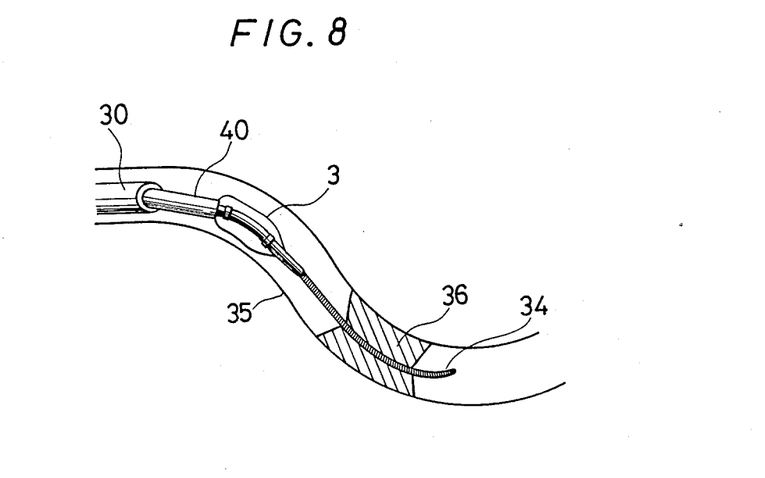
Figure 9:
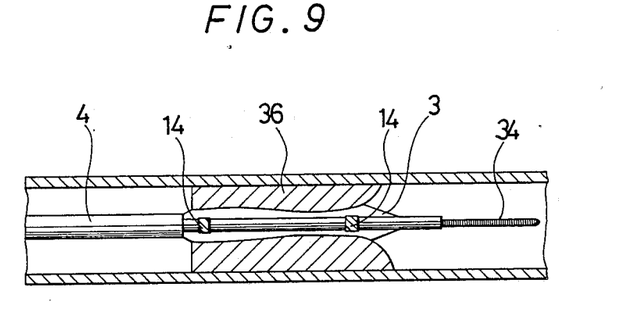
Figure 10:
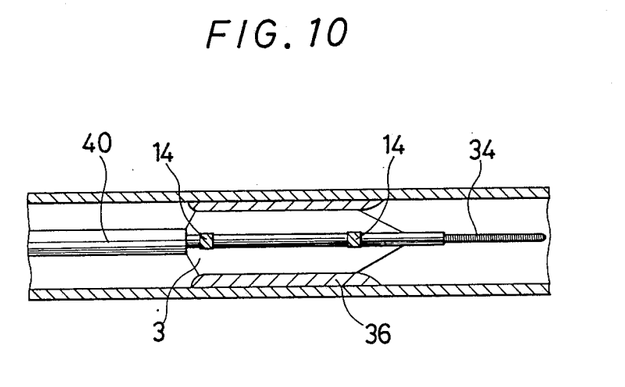

Upon inserting the catheter 40 equipped with the expansible member into a blood vessel, at first, an inflow portion for the blood vessel is insured in the human body by means of Seldinger method or the like, a guide wire for guide catheter (not shown) is then retained in the blood vessel, the guide catheter 30 is inserted into the blood vessel 35 along it, as shown in FIG. 7, the guide catheter 30 is retained in the inlet 32 of the carronary artery including an aimed lesion part, and the guide wire for the guide catheter is withdrawn. As shown in FIG. 6, the catheter 40 equipped with the expansible member according to the present invention into which a guide wire 34 for catheter equipped with expansible member is inserted, is inserted through a Y-shaped connector 50 disposed at the rear end of the guide catheter 30. Insertion into the blood vessel is conducted in a state that the guide wire 34 for catheter equipped with expansible member is protruded beyond the tip of the catheter 40 equipped with the expansible member by several centimeters. The catheter 40 equipped with the expansible member advances in the guide catheter 30 and as shown in FIG. 8, enters in the blood vessel 35 including the aimed lesion part by leaving the tip of the guide catheter 30. The guide wire 34 for catheter equipped with expansible member is advanced to the aimed lesion part, passed through the stricture portion 36 and then retained. The catheter 40 equipped with the expansible member is advanced in the blood vessel 35 along the guide wire 34 for catheter equipped with expansible member. After the catheter 40 equipped with the expansible member reaches a position near the stricture portion 36, the expansible member 3 is positioned in the stricture portion 36 under X-ray perspection by using the X-ray impermeable markers 14 disposed on the inner tube 1 as reference marks as shown in FIG. 9. Subsequently, vasographic contrast liquid is injected at a pressure from several atmospheres to ten and several atmospheres by means of an injector 54 equipped with a pressure gauge connected to the third opening 11 forming the injection port of the catheter 40 equipped with the expansible member shown in FIG. 6 to compress and expand the stricture portion 36 as shown in FIG. 10. The contrast liquid is injected through a contrast liquid injection port 52 of the Y-shaped connector 50 of the guide catheter 30 shown in FIG. 6 to confirm the state of blood stream on the peripheral side by the X-ray perspection. When an improvement of the blood flow on the peripheral side is recognized, the catheter 40 equipped with the expansible member and the guide wire 34 for catheter equipped with expansible member are withdrawn and then the guide catheter is withdrawn and blood is stopped under pressure to complete the operation.

INDUSTRIAL APPLICABILITY

Since a catheter equipped with an expansible member according to the present invention comprises an inner tube having a first lumen whose tip is open and a second lumen extending to the tip direction of the first lumen, an outer tube disposed coaxially with said inner tube and disposed at a position recessed by a predetermined distance from the tip of said inner tube and forming a third lumen between it and the outer surface of said inner tube, a contractible or foldable expansible member having a tip end portion and a base end portion, said base end portion being fitted to said outer tube and said tip end portion being fitted to said inner tube, said expansible member communicating with said second lumen near said tip end portion and with said third lumen near said base end portion, a first opening communicating with said first lumen and a second opening communicating with said second lumen disposed at the base end portion of said inner tube, and a third opening each disposed at the base end portion of said outer tube and communicating with said third lumen, especially, the third lumen is in communication with a portion near the base end portion of the expansible member and the second lumen is in communication with a portion near the tip end portion of the expansible member, when expansion fluid for the expansible member is injected through the third lumen, air within the third lumen and further within the expansible member is replaced by the injected fluid in accordance with the inflow of the fluid and the air can be made to flow through the second lumen and the second opening to the outside. Therefore, the air within the catheter can be easily and surely removed. Moreover, since the third lumen which is in communication with the portion near the base end portion of the expansible member and through which expansion fluid for the expansible member is injected is formed between the inner tube and the outer tube, the third lumen has a relatively large volume so the expansion fluid can be easily injected even if it has a large flow resistance, for example, in the case of vasographic contrast liquid. Furthermore, since no metal pipe or the like is used for removing air from the inside of the expansible member, there is no worry that the catheter or expansible member is damaged.

We claim:

1. A catheter equipped with an expansible member comprising an inner tube having a first lumen whose tip is open and a second lumen extending to the tip direction of the first lumen; an outer tube disposed coaxially with said inner tube and having a tip at a position recessed by a predetermined distance from the tip of said inner tube and forming a third lumen between it and the outer surface of said inner tube; a contractible or foldable expansible member having a tip end portion and a base end portion, said base end portion being fitted to said outer tube and said tip end portion being fitted to said inner tube, said expansible member communicating with said second lumen near said tip end portion and with said third lumen near said base end portion; a first opening communicating with said first lumen and a second opening communicating with said second lumen each disposed at the base end portion of said inner tube; and a third opening disposed at the base end portion of said outer tube and communicating with said third lumen.

2. A catheter equipped with an expansible member according to claim 1, wherein said first, second and third openings are disposed in a branched hub attached to the base ends of said inner tube and said outer tube.

* * * * *